US00PP33374P3

(12) United States Plant Patent
van Sambeek

(10) Patent No.: US PP33,374 P3
(45) Date of Patent: Aug. 17, 2021

(54) ***PHLOX* PLANT NAMED 'DOPHLFLALIPIIM'**

(50) Latin Name: *Phlox paniculata*
Varietal Denomination: Dophlflalipiim

(71) Applicant: DUMMEN GROUP B.V., De Lier (NL)

(72) Inventor: Ellen van Sambeek, Oegstgeest (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 17/037,049

(22) Filed: Sep. 29, 2020

(65) Prior Publication Data

US 2021/0100148 P1 Apr. 1, 2021

Related U.S. Application Data

(60) Provisional application No. 62/973,349, filed on Sep. 30, 2019.

(51) Int. Cl.
*A01H 5/02* (2018.01)
*A01H 6/70* (2018.01)

(52) U.S. Cl.
USPC ..... Plt./320
CPC ..... *A01H 6/70* (2018.05)

(58) Field of Classification Search
USPC ..... Plt./320
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Phlox* plant named 'Dophlflalipiim', characterized by its upright and uniform plant habit; vigorous growth habit; early and freely flowering habit; dense inflorescences with reddish purple-colored flowers with white-colored centers; and good garden performance.

1 Drawing Sheet

Botanical designation: *Phlox paniculata.*
Cultivar denomination: 'DOPHLFLALIPIIM'.

CROSS-REFERENCED TO CLOSELY RELATED APPLICATIONS

Title: Varieties of *Phlox* Plants
Inventor: Ellen van Sambeek
Applicant: Dümmen Group B.V.
Provisional application Ser. No. 62/973,349
Filed: Sep. 30, 2019
Inventor and Applicant hereby claim the benefit of this provisional U.S. Patent Application.

STATEMENT REGARDING PRIOR DISCLOSURES BY INVENTOR & APPLICANT/ASSIGNEE

An European Community Plant Breeder's Rights application for the instant plant was filed by the Applicant/Assignee, Dümmen Group B.V. of De Lier, The Netherlands on Sep. 19, 2019, application number 2019/2282. Foreign priority is not claimed to this application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Phlox* plant, botanically known as *Phlox paniculata* and hereinafter referred to by the name 'Dophlflalipiim'.

The new *Phlox* plant is a product of a planned breeding program conducted by the Inventor in Aalsmeer, The Netherlands. The objective of the breeding program was to create new early and freely-flowering *Phlox* plants with attractive flower color.

The new *Phlox* plant originated from a cross-pollination made by the Inventor in July, 2014 in Aalsmeer, The Netherlands, of a proprietary selection of *Phlox paniculata* identified as code number PA09-000103-007, not patented, as the female, or seed, parent with a proprietary selection of *Phlox paniculata* identified as code number PA-0099, not patented, as the male, or pollen, parent. The new *Phlox* plant was discovered and selected by the Inventor as a single flowering plant from within the progeny of the stated cross-pollination in a controlled environment in Aalsmeer, The Netherlands in July, 2015.

Asexual reproduction of the new *Phlox* plant by vegetative cuttings in a controlled environment in Aalsmeer, The Netherlands since March, 2016 has shown that the unique features of this new *Phlox* plant are stable and reproduced true to type in successive generations.

SUMMARY OF THE INVENTION

Plants of the new *Phlox* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Dophlflalipiim'. These characteristics in combination distinguish 'Dophlflalipiim' as a new and distinct *Phlox* plant:

1. Upright and uniform plant habit.
2. Vigorous growth habit.
3. Early and freely flowering habit.
4. Dense inflorescences with reddish purple-colored flowers with white-colored centers.
5. Good garden performance.

Plants of the new *Phlox* differ primarily from plants of the female parent selection in flower color as plants of the new *Phlox* have reddish purple-colored flowers with white-colored centers whereas plants of the female parent selection have lilac-colored flowers.

Plants of the new *Phlox* differ primarily from plants of the male parent selection in plant habit as plants of the new *Phlox* are more uniform than plants of the male parent selection.

Plants of the new *Phlox* can be compared to plants of *Phlox paniculata* 'Sweet Summer Snow', not patented. In side-by-side comparisons, plants of the new *Phlox* and 'Sweet Summer Snow' differ in the following characteristics:

1. Plants of the new *Phlox* are more compact than plants of 'Sweet Summer Snow'.
2. Plants of the new *Phlox* have smaller leaves than plants of 'Sweet Summer Snow'.
3. Plants of the new *Phlox* are more freely flowering than plants of 'Sweet Summer Snow'.
4. Plants of the new *Phlox* flower about two weeks earlier than plants of 'Sweet Summer Snow'.
5. Plants of the new *Phlox* and 'Sweet Summer Snow' differ in flower color as plants of the new *Phlox* have reddish purple-colored flowers with white-colored centers whereas plants of 'Sweet Summer Snow' have white-colored flowers.

BRIEF DESCRIPTION OF THE PHOTOGRAPH

The accompanying colored photograph illustrates the overall appearance of the new *Phlox* plant showing the colors as true as it is reasonably possible to obtain in colored reproductions of this type. Colors in the photograph may differ slightly from the color values cited in the detailed botanical description which accurately describe the colors of the new *Phlox* plant.

The photograph comprises a side perspective view of typical flowering plant of 'Dophlflalipiim' grown in a container.

DETAILED BOTANICAL DESCRIPTION

The aforementioned photograph and following observations, measurements and values describe plants grown during the early summer in 17-cm containers initially in a glass-covered greenhouse and finished in an outdoor nursery in Aalsmeer, The Netherlands and under cultural practices typical of commercial *Phlox* production. During the production of the plants, day temperatures averaged 21° C. and night temperatures averaged 15° C. Plants were pinched one time one week after planting rooted young plants and were twelve weeks old when the photograph and the description were taken. In the following description, color references are made to The Royal Horticultural Society Colour Chart, 2001 Edition, except where general terms of ordinary dictionary significance are used.

Botanical classification: *Phlox paniculata* 'Dophlflalipiim'.

Parentage:

*Female, or seed, parent*.—Proprietary selection of *Phlox paniculata* identified as code number PA09-000103-007, not patented.

*Male, or pollen, parent*.—Proprietary selection of *Phlox paniculata* identified as code number PA-0099, not patented.

Propagation:

*Type*.—By vegetative cuttings.

*Time to initiate roots, summer*.—About 16 days at temperatures about 26° C.

*Time to initiate roots, winter*.—About three weeks at temperatures about 23° C.

*Time to produce a rooted young plant, summer*.—About 24 days at temperatures about 23° C.

*Time to produce a rooted young plant, winter*.—About four weeks at temperatures about 18° C.

*Root description*.—Thick, fibrous; typically white in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Herbaceous perennial typically grown as a container and garden plant; upright and uniform plant habit; vigorous growth habit and rapid growth rate.

*Plant height*.—About 36 cm.

*Plant width* (*spread*).—About 30 cm.

*Lateral branches*.—Branching habit: About two or three lateral branches develop after pinching. Length: About 30 cm. Internode length: About 4 cm. Strength: Strong. Aspect: Mostly upright. Texture: Fine pubescence. Color: Close to 141A; at the nodes, tinged with close to 187A.

Leaf description:

*Arrangement*.—Opposite, simple.

*Length*.—About 6.5 cm.

*Width*.—About 2.7 cm.

*Shape*.—Ovate to elliptical.

*Apex*.—Acuminate.

*Base*.—Cuneate.

*Margin*.—Entire.

*Texture, upper and lower surfaces*.—Smooth, glabrous.

*Venation pattern*.—Pinnate, reticulate.

*Color*.—Developing leaves, upper surface: Close to 137A. Developing leaves, lower surface: Close to 138A. Fully expanded leaves, upper surface: Close to 139A; venation, close to 138A. Fully expanded leaves, lower surface: Close to 137B; venation, close to 138D.

*Petioles*.—Length: About 1 mm. Diameter: About 2 mm. Strength: Strong, flexible. Texture, upper and lower surfaces: Smooth, glabrous. Color, upper surface: Close to 138A. Color, lower surface: Close to 138D.

Flower description:

*Flower type and flowering habit*.—Single rotate and salverform flowers arranged in compound terminal and lateral panicles; flowers face mostly upright to outwardly depending on position on inflorescence; freely flowering habit with about 32 to 37 flowers per inflorescence and about 430 flowers developing per plant during the flowering season.

*Fragrance*.—Slightly fragrant, pleasant.

*Natural flowering season*.—Early flowering habit, plants begin flowering about ten weeks after planting; plants flower in July in the garden in The Netherlands; flowers not persistent.

*Flower buds*.—Height: About 3 cm. Diameter: About 6 mm. Shape: Conical. Color: Close to 87A.

*Inflorescence height*.—About 23 cm.

*Inflorescence diameter*.—About 17 cm.

*Flower diameter*.—About 3.2 cm.

*Flower depth*.—About 2.7 cm.

*Flower throat diameter*.—About 3 mm.

*Flower tube length*.—About 2 cm.

*Flower diameter, proximally*.—About 3 mm.

*Petals*.—Quantity per flower: Typically five in a single whorl; petals fused at the base into a narrow tube. Lobe length: About 1.5 cm. Lobe width: About 1.7 cm. Lobe shape: When flattened, round. Lobe apex: Rounded. Lobe margin: Entire. Lobe texture, upper and lower surfaces: Smooth, glabrous. Throat texture: Slightly rough; distally, glabrous and proximally, pubescent. Tube texture: Pubescent. Color: When opening and fully opened, upper surface: Close to 74A; towards throat, close to 155C; venation, close to 74A and 155C; color does not change with development. When opening and fully opened, lower surface: Close to 73B; venation, close to 73A; color does not change with development. Throat: Close to 78A; venation, close to 78D. Tube: Close to 78A; venation, close to 78D.

*Sepals*.—Quantity per flower: Typically five in a single whorl, fused towards the base; calyx, campanulate. Length: About 1.1 cm. Width: About 2 mm. Shape: Narrowly deltoid. Apex: Acuminate. Margin: Entire. Texture, upper and lower surfaces: Smooth, glabrous. Color: When opening and fully opened, upper surface: Close to 79A. When opening and fully opened, lower surface: Close to 143A.

*Peduncles*.—Length: About 10 cm. Diameter: About 2 mm. Strength: Moderately strong. Aspect: About 30° from lateral branch axis. Texture: Fine pubescence. Color: Close to 143A occasionally tinged with close to 187A.

*Pedicels*.—Length: About 3 cm. Diameter: About 2 mm. Strength: Moderately strong. Aspect: About 45° from peduncle axis. Texture: Fine pubescence. Color: Close to 143A occasionally tinged with close to 187A.

*Reproductive organs*.—Stamens: Quantity per flower: Typically five. Filament length: About 1 mm. Filament color: Close to 155C. Anther length: About 2 mm. Anther color: Close to 2D. Pollen amount: Moderate. Pollen color: Close to 155C. Pistils: Quantity per flower: One. Pistil length: About 2.5 cm. Stigma shape: Cleft, three-parted. Stigma color: Close to 150C. Style length: About 2 cm. Style color: Close to 84A. Ovary color: Close to 143A.

*Seeds and fruits*.—To date, seed and fruit development have not been observed on plants of the new *Phlox*.

Garden performance: Plants of the new *Phlox* have been observed to have good garden performance and to tolerate rain, wind and temperatures ranging from −20° C. to 35° C.

Pathogen & pest resistance: To date, plants of the new *Phlox* have not been observed to be resistant to pathogens and pests common to *Phlox* plants.

It is claimed:

1. A new and distinct *Phlox* plant named 'Dophlflalipiim' as illustrated and described.

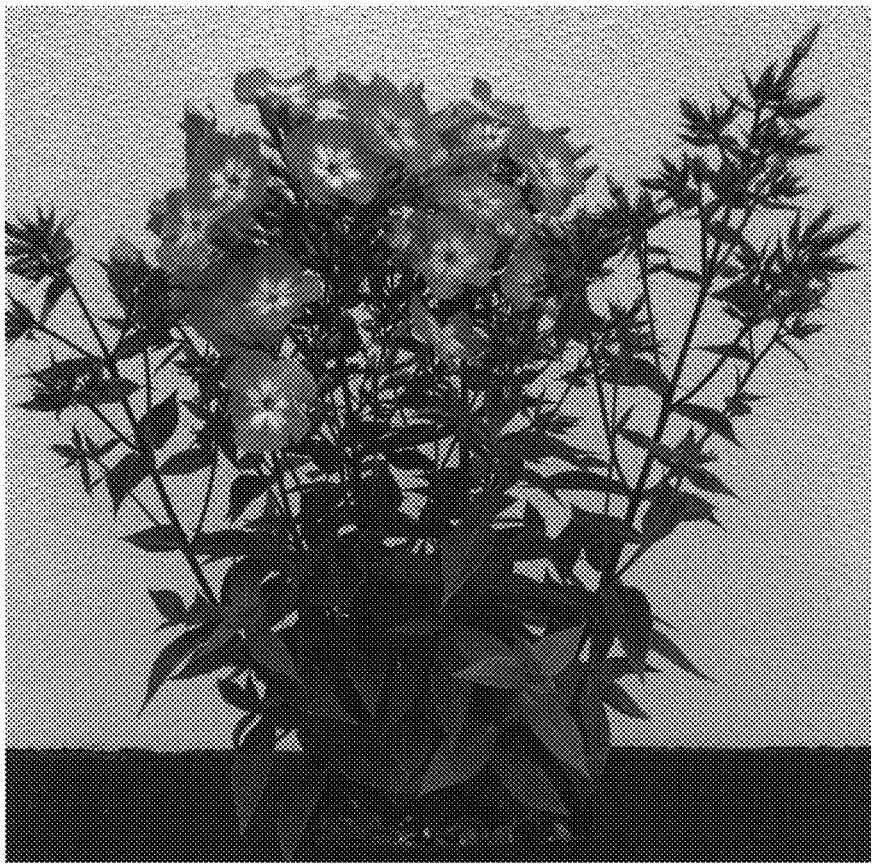

* * * * *